(12) United States Patent
Son et al.

(10) Patent No.: US 12,053,653 B2
(45) Date of Patent: Aug. 6, 2024

(54) FOCUSED ULTRASOUND DEVICE AND METHOD FOR SETTING ORDER OF FOCUSED ULTRASOUND TREATMENT THEREOF

(71) Applicant: IMGT CO., LTD., Seongnam-si (KR)

(72) Inventors: Keon Ho Son, Seongnam-si (KR); Dae Seung Kim, Seoul (KR); Jun Hyeok Jang, Incheon (KR)

(73) Assignee: IMGT CO., LTD., Seongnam-si (KR)

( * ) Notice: Subject to any disclaimer, the term of this patent is extended or adjusted under 35 U.S.C. 154(b) by 0 days.

(21) Appl. No.: 18/269,733

(22) PCT Filed: Feb. 24, 2021

(86) PCT No.: PCT/KR2021/002282
§ 371 (c)(1),
(2) Date: Jun. 26, 2023

(87) PCT Pub. No.: WO2022/149652
PCT Pub. Date: Jul. 14, 2022

(65) Prior Publication Data
US 2024/0050773 A1 Feb. 15, 2024

(30) Foreign Application Priority Data
Jan. 5, 2021 (KR) .................. 10-2021-0000782

(51) Int. Cl.
*A61N 7/00* (2006.01)
*G16H 20/40* (2018.01)
*G16H 40/60* (2018.01)

(52) U.S. Cl.
CPC .............. *A61N 7/00* (2013.01); *G16H 20/40* (2018.01); *G16H 40/60* (2018.01); *A61N 2007/0052* (2013.01)

(58) Field of Classification Search
CPC .............. A61N 7/00; A61N 2007/0052; A61N 2007/0082; A61N 7/02; A61N 2007/025;
(Continued)

(56) References Cited

U.S. PATENT DOCUMENTS

| 5,485,839 A | 1/1996 | Aida et al. |
| 5,643,179 A | 7/1997 | Fujimoto |
| 6,618,620 B1 | 9/2003 | Freundlich et al. |
| 7,699,780 B2 | 4/2010 | Vitek et al. |
| 9,573,000 B2 | 2/2017 | Albright et al. |

(Continued)

FOREIGN PATENT DOCUMENTS

| CN | 1293926 C | 1/2007 |
| JP | H05-300910 A | 11/1993 |

(Continued)

OTHER PUBLICATIONS

Office Action Issued Aug. 9, 2022 in counterpart Korean Patent Application KR 10-2021-0000782. (7 Pages in Korean).

(Continued)

*Primary Examiner* — Hien N Nguyen
(74) *Attorney, Agent, or Firm* — NSIP Law

(57) ABSTRACT

Disclosed are a focused ultrasound device and a method for setting an order of focused ultrasound treatment thereof. When using an ultrasound treatment method using mechanical energy, the focused ultrasound device according to an embodiment determines a next focal point position in consideration of at least one previous focal point position of focused ultrasound and thus can minimize thermal increase of an affected area and maximally utilize the mechanical energy.

12 Claims, 8 Drawing Sheets

(58) Field of Classification Search
CPC ........ G16H 20/40; G16H 40/60; A61B 8/469;
A61B 8/483; A61B 8/085; A61B 8/54
See application file for complete search history.

(56) References Cited

U.S. PATENT DOCUMENTS

| | | | |
|---|---|---|---|
| 9,623,267 | B2 | 4/2017 | Ulric et al. |
| 9,937,364 | B2 | 4/2018 | Kohler |
| 11,241,218 | B2* | 2/2022 | Emery ............... A61B 8/54 |
| 2006/0058671 | A1 | 3/2006 | Vitek et al. |
| 2010/0249669 | A1 | 9/2010 | Ulric et al. |
| 2011/0208055 | A1 | 8/2011 | Dalal et al. |
| 2012/0046592 | A1 | 2/2012 | Albright et al. |
| 2013/0018285 | A1 | 1/2013 | Park et al. |
| 2014/0018709 | A1 | 1/2014 | Ahn et al. |
| 2014/0277032 | A1 | 9/2014 | Ahn et al. |
| 2015/0065922 | A1 | 3/2015 | Kohler |
| 2019/0038171 | A1* | 2/2019 | Howard ............... A61B 5/24 |
| 2022/0096174 | A1* | 3/2022 | Harlev ............... A61B 34/10 |
| 2022/0117668 | A1* | 4/2022 | Qin ............... A61B 34/20 |

FOREIGN PATENT DOCUMENTS

| | | |
|---|---|---|
| JP | H07-184907 A | 7/1995 |
| JP | H08-84740 A | 4/1996 |
| JP | 2008-509713 A | 4/2008 |
| KR | 10-2011-0029630 A | 3/2011 |
| KR | 10-2011-0121701 A | 11/2011 |
| KR | 10-2013-0009138 A | 1/2013 |
| KR | 10-2014-0008103 A | 1/2014 |
| KR | 10-2014-0113172 A | 9/2014 |
| KR | 10-2087281 B1 | 3/2020 |
| RU | 2 657 950 C2 | 6/2018 |

OTHER PUBLICATIONS

Office Action Issued Dec. 26, 2022 in Counterpart Korean Patent Application KR 10-2021-0000782 (2 Pages in Korean).
Russian Office Action and search report issued on Nov. 30, 2023, in counterpart Russian Patent Application No. 2023120476/14 (11 pages in English).
Korean Office Action issued on Aug. 9, 2022 in corresponding Korean Patent Application No. 10-2021-0000782. (7 pages in Korean and 9 pages in English).
Korean Decision to Grant a Patent issued on Dec. 26, 2022 in corresponding Korean Patent Application No. 10-2021-0000782. (2 pages in Korean and 2 pages in English).
Japanese Office Action issued on May 7, 2024, in counterpart Japanese Patent Application No. 2023-540153 (5 pages in English, 3 pages in Japanese).

* cited by examiner

FOCUSED ULTRASOUND DEVICE AND METHOD FOR SETTING ORDER OF FOCUSED ULTRASOUND TREATMENT THEREOF

CROSS REFERENCE TO RELATED APPLICATIONS

This application is a U.S. National Stage Application of International Application No. PCT/KR2021/002282, filed on Feb. 24, 2021, which claims the benefit under 35 USC 119(a) and 365(b) of Korean Patent Application No. 10-2021-0000782, filed on Jan. 5, 2021, in the Korean Intellectual Property Office, the entire disclosure of which is incorporated herein by reference for all purposes.

TECHNICAL FIELD

The present invention relates to diagnosis and treatment technology using ultrasound, and more particularly, to image scanning and treatment technology using focused ultrasound (FUS) for image guided therapy.

The present invention was made based on the Korean National Project. Information on the above Korean National Project includes the following: NTIS series number: 9991006682, project number: 202011B03-01, department name the Ministry of Science and Information & Communication Technology, the Ministry of Trade, Industry, and Energy, and the Ministry of Health and Welfare, the Ministry of Food and Drug Safety, research project name: Collaborative Life-Cycle Medical Device R&D Project, research project name Development of Commercialization of Market-Leading Ultrasound Image-Guided, High-Intensity Focused Ultrasound Treatment Device for Integrated Therapy for Pancreatic Cancer, research management institution: Korea Medical Device Development Fund, contribution rate: 100%, research supervising institute: IMGT. Co., Ltd., research period: 1, Sep. 2020-28, Feb. 2021.

BACKGROUND ART

Ultrasound signals may be used in the treatment of biological tissues, such as cancer, tumors, lesions, and the like. Treatment with ultrasound is a method of treating a lesion by emitting ultrasound signals to the lesion of the human body. Ultrasound treatment may cause less trauma of a patient, compared to general surgical treatment or chemotherapy, and realize non-invasive treatment. Examples of the application of ultrasound treatment include liver cancer, bone sarcoma, breast cancer, pancreatic cancer, kidney cancer, soft tissue tumors, pelvic tumors, and the like.

DISCLOSURE

Technical Problem

According to an embodiment, there are proposed a focused ultrasound device which can minimize thermal increase of an affected area and maximally utilize mechanical energy when an ultrasound treatment method is used for the purpose of stimulating the affected area or improving the delivery effect of a therapeutic drug by using mechanical energy rather than thermal therapy, and a method for setting a focused ultrasound treatment sequence thereof.

Technical Solution

A method for setting a focused ultrasound treatment sequence according to an embodiment includes: arranging treatment point candidates within a three-dimensional structure in a coordinate system, determining a position of a treatment point to be irradiated with focused ultrasound, determining a position of a next treatment point, wherein, if there is at least one previous treatment point irradiated with focused ultrasound, the position of the next treatment point is determined among the treatment point candidates in consideration of a position of the at least one previous treatment point, and emitting focused ultrasound to the determined position of the next treatment point.

The previous treatment point may be the latest treatment point $PT(0)_n$. The previous treatment point may include the latest treatment point $PT(0)_n$ and first to Lth treatment points (L=integer) preceding the latest treatment point $PT(0)_n$, L may be preset and be changeable by a user, and a different weight may be assigned to each treatment point.

In the determining of the position of the next treatment point, a candidate treatment point with the farthest distance from a previous treatment point may be determined as the next treatment point from among a plurality of treatment point candidates.

In the determining of the position of the next treatment point, when there are a plurality of treatment point candidates with the farthest distance from the previous treatment point, a treatment point candidate at a position with the shortest driving distance of a device may be determined as the next treatment point.

In the determining of the position of the next treatment point, after presetting a maximum distance of the next treatment point with respect to the previous treatment point, the position of the next treatment point may be determined within the preset maximum distance.

The determining of the position of the next treatment point may include converting distance information between a previous treatment point and next treatment points into temperature information and determining a treatment point candidate at a position having a minimum temperature increase as the next treatment point from among next treatment point candidates.

The determining of the position of the next treatment point may include calculating a distance value $$\begin{bmatrix} D(0)_{n+1} & \cdots & D(0)_{n+m} \\ \vdots & \ddots & \vdots \\ D(L)_{n+1} & \cdots & D(L)_{n+m} \end{bmatrix},$$

calculating a maximum distance $[D(0)_{max}, \ldots, D(L)_{max}]$, and determining a position having a maximum value max $[W(0)*D(0)_{max}+ \ldots +, W(L)*D(L)_{max}]$ as the position of the next treatment point, wherein $[D(0)_{n+1}, \ldots, D(0)_{n+m}]$ may be a distance between the latest treatment point $PT(0)n$ and each of the next treatment point candidates $[PT_{n+1}, \ldots, PT_{n+m}]$, $[D(L)_{n+1}, \ldots, D(L)_{n+m}]$ may be a distance between an Lth treatment point $PT(L)_n$, preceding the latest treatment point $PT(0)_n$, and each of the next treatment point candidates $[PT_{n+1}, \ldots, PT_{n+m}]$, $D(0)$max may be $\max[D(0)_{n+1}, \ldots, D(0)_{n+m}]$, $D(L)$max may be $\max[D(L)_{n+1}, \ldots, D(L)_{n+m}]$, $W(0), \ldots, W(L)$ may each be a weight, and L may represent an Lth irradiation before the latest treatment point $PT(0)_n$.

The determining of the position of the next treatment point may include calculating a distance value $$\begin{bmatrix} D(0)_{n+1} & \cdots & D(0)_{n+m} \\ \vdots & \ddots & \vdots \\ D(L)_{n+1} & \cdots & D(L)_{n+m} \end{bmatrix},$$

calculating a temperature value $$\begin{bmatrix} T_\delta D(0)_{n+1} & \cdots & T_\delta D(0)_{n+m} \\ \vdots & \ddots & \vdots \\ T_\delta D(L)_{n+1} & \cdots & T_\delta D(L)_{n+m} \end{bmatrix}$$

converted from the distance value, calculating a maximum temperature $[T_{max(n+1)}, \ldots, T_{max(n+m)}]$, and determining a position having a minimum value $Min[T_{max(n+1)}, T_{max(n+2)}, T_{max(n+3)}, \ldots, T_{max(n+m)}]$ as the position of the next treatment point, wherein $[D(0)_{n+1}, \ldots, D(0)_{n+m}]$ may be a distance between the latest treatment point $PT(0)_n$ and each of the next treatment point candidates $[PT_{n+1}, \ldots, PT_{n+m}]$, $[D(L)_{n+1}, \ldots, D(L)_{n+m}]$ may be a distance between an Lth treatment point $PT(L)_n$ preceding the latest treatment point $PT(0)_n$, and each of the next treatment point candidates $[PT_{n+1}, \ldots, PT_{n+m}]$, $T_{max(n+1)}$ may be a maximum value $max[T_\delta D(0)_{n+1}, \ldots, T_\delta D(0)_{n+m}]$, $T_{max(n+m)}$ may be a maximum value $max[T_\delta D(L)_{n+1}, \ldots, T_\delta D(L)_{n+m}]$, $T_\delta$ may be a temperature change value during an irradiation time δt, and L may represent an Lth irradiation before the latest treatment point $PT(0)_n$.

The determining of the position of the next treatment point may further include, if a temperature change value is less than a preset temperature value when the determined next treatment point is irradiated with focused ultrasound, ultimately determining the irradiated treatment point as the next treatment point.

The method for setting a focused ultrasound treatment sequence may further include adjusting treatment parameters to minimize thermal damage to a target region when focused ultrasound is intensively focused on the same treatment point.

A focused ultrasound device according to another embodiment includes a control unit configured to arrange treatment point candidates within a three-dimensional structure in a coordinate system and, if there is at least one previous treatment point irradiated with focused ultrasound, determine a position of a next treatment point among the treatment point candidates in consideration of a position of the at least one previous treatment point, and a transceiver unit configured to emit focused ultrasound to the determined position of the treatment point.

The control unit may determine a treatment point candidate with the farthest distance from a previous treatment point as the next treatment point from among a plurality of treatment point candidates.

When there are a plurality of treatment point candidates with the farthest distance from the previous treatment point, the control unit may determine a treatment point candidate at a position with the shortest driving distance of a device as the next treatment point.

The control unit may preset a maximum distance of the next treatment point with respect to a previous treatment point, and then determine the position of the next treatment point within the preset maximum distance.

The control unit may convert distance information between a previous treatment point and a group of next treatment point candidates into temperature information and determine a treatment point candidate at a position having a minimum temperature increase, from among the next treatment point candidates, as the next treatment point by using the converted temperature information.

The controller may adjust treatment parameters to minimize thermal damage to a target region when focused ultrasound is intensively focused on a predetermined treatment point.

Advantageous Effects

According to a focused ultrasound device and a method for setting a focused ultrasound treatment sequence thereof in accordance with the present invention, when using an ultrasound treatment method for the purpose of simulating the affected area or improving the delivery effect of a therapeutic drug by using mechanical energy, rather than thermal therapy, it is possible to minimize thermal increase of an affected area and maximally utilize the mechanical energy.

For example, a next treatment point position is determined in consideration of at least one previous treatment point position of focused ultrasound and thus thermal increase in an affected area can be minimized. Further, when there are a plurality of treatment point candidates with the farthest distance from a previous treatment point, a treatment point candidate at a position with the shortest driving distance of the device may be determined as the next treatment point, thereby minimizing the movement of the device.

The present invention has simple implementation and operation principle and is scalable, such that it is applicable not only to the field of focused ultrasound but also to applications minimizing radiation exposure or dose of similar energy.

MODES OF THE INVENTION

Figure 1:
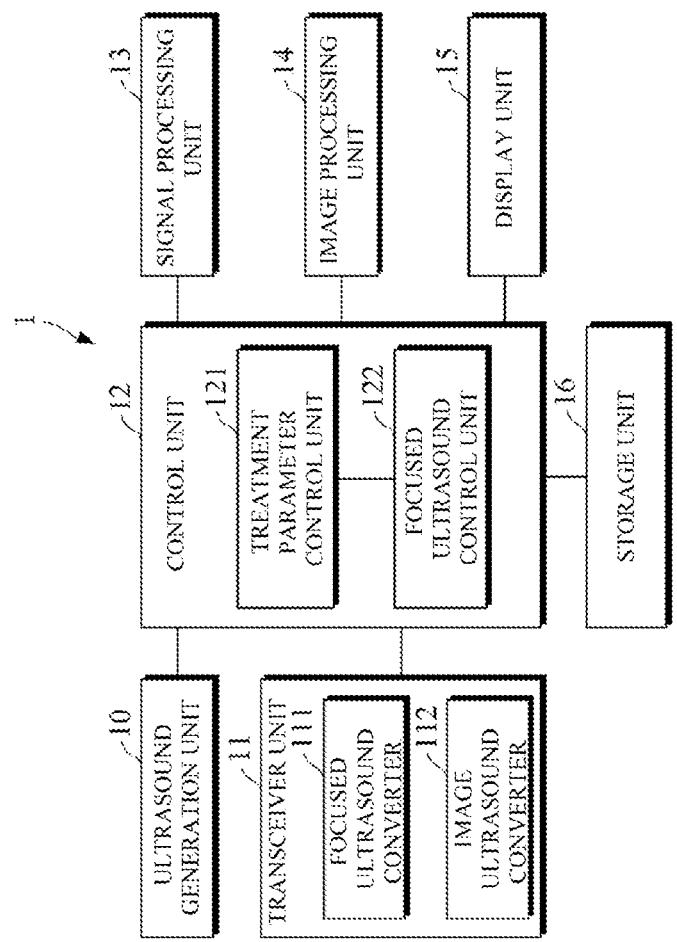
FIG. 1 is a block diagram illustrating the configuration of a focused ultrasound device according to an embodiment of the present invention.

Advantages and features of the present invention and methods of achieving the same will be clearly understood with reference to the accompanying drawings and embodiments described in detail below. However, the present invention is not limited to the embodiments to be disclosed below but may be implemented in various different forms. The embodiments are provided in order to fully explain the present embodiments and fully explain the scope of the present invention for those skilled in the art. The scope of the present invention is only defined by the appended claims. Like reference numerals refer to like elements throughout the specification.

In addition, when the embodiments of the present invention are described, if it is determined that detailed descriptions of known technology related to the present invention unnecessarily obscure the subject matter of the present invention, detailed descriptions thereof will be omitted. Some terms described below are defined by considering functions in the present invention, and meanings may vary depending on, for example, a user or operator's intentions or customs. Therefore, the meanings of terms should be interpreted based on the scope throughout this specification.

In this case, it will be appreciated that each block of block diagrams and combinations of steps of flowcharts may be performed by computer program instructions (an execution engine). Since the computer program instructions may be loaded into a processor of a general-purpose computer, special purpose computer, or other programmable data processing devices, the instructions executed through the processor of the computer or other programmable data processing devices generate a means for performing the functions described in the block(s) of the block diagrams or the step(s) of the flowcharts.

Since the computer program instructions may be stored in a computer usable or computer readable memory that can be directed to a computer or other programmable data processing devices to implement functionality in a particular manner, the instructions stored in the computer usable or computer readable memory may produce a manufactured item containing an instruction means for performing the functions described in the block(s) of the block diagrams or the step(s) of the flowcharts.

Since the computer program instructions may also be installed in a computer or other programmable data processing devices, instructions for performing a series of operating steps on a computer or other programmable data processing devices to generate a computer-implemented process to be performed on the computer or other programmable data processing devices may provide steps for performing the functions described in the block(s) of the block diagrams or the step(s) of the flowcharts.

In addition, each block or step may represent a module, segment, or portion of code that includes one or more executable instructions for executing a specified logical function(s). It should also be noted that in some alternative implementations, the functions mentioned in the blocks or steps may occur out of order. For example, two blocks or steps illustrated in succession may in fact be executed substantially concurrently or the blocks may sometimes be executed in reverse order depending on the corresponding function.

Hereinafter, embodiments of the present invention will be described in detail with reference to the accompanying drawings. However, the present invention may be realized in various forms, and the scope of the present invention is not limited to such embodiments. The embodiments of the present invention are provided to aid those skilled in the art in the explanation and the understanding of the present invention.

FIG. 1 is a block diagram illustrating the configuration of a focused ultrasound device according to an embodiment of the present invention.

Treatment using focused ultrasound (FUS) is mainly used for thermal therapy by increasing temperature of an affected area, treatment using mechanical energy, and the like. Thermal therapy, one of the representative treatment methods, is a thermal ablation of a lesion to cause necrosis of the lesion. However, the thermal therapy is likely to cause side effects due to thermal increase in surrounding normal tissue.

A focused ultrasound device 1 according to an embodiment uses focused ultrasound, rather than thermal therapy, for the purpose of stimulating an affected area or improving delivery effect of a therapeutic drug by using mechanical energy. The present invention proposes a focused ultrasound device capable of minimizing thermal increase in an affected area and maximally utilizing mechanical energy when using an ultrasound treatment method using the mechanical energy, and a method for setting a focused ultrasound treatment sequence thereof.

Referring to FIG. 1, the focused ultrasound device 1 includes an ultrasound generation unit 10, a transceiver unit 11, a control unit 12, a signal processing unit 13, an image processing unit 14, a display unit 15, and a storage unit 16.

The transceiver unit 11 may include a focused ultrasound converter 111 operable to transmit focused ultrasound for treatment and an image ultrasound converter 112 operable to transmit and receive diagnostic ultrasound. The focused ultrasound converter 111 converts an electrical signal with short pulses, which is a driving signal received from the ultrasound generation unit 10, into focused ultrasound and transmits the same to a target region of tissue.

The image ultrasound converter 112 converts an electrical signal with short pulses, which is a driving signal received from the ultrasound generation unit 10, into image ultrasound, transmits the image ultrasound to the target region of tissue, and extracts an echo signal reflected from the target region.

The signal processing unit 13 processes the received ultrasound echo signal and transmits the processed signal to the image processing unit 14. The signal processing unit 13 may include a low noise amplifier (LAN) and an analog-to-digital (A/D) converter (ADC). The image processing unit 14 allows an image to be produced based on a reception signal, which is signal-processed by the signal processing unit 13, and outputs an ultrasound image through the display unit 15. The storage unit 16 stores the reception signal formed by the transceiver unit 11 and stores information necessary for operation of the control unit 12. After confirming an affected area from the ultrasound image output through the display unit 15, a site to be treated may be set. The ultrasound image may be a three-dimensional multi-plane image. The site to be treated may be automatically set, or manually set by a user.

The control unit 12 controls the overall operation of the focused ultrasound device 1. The control unit 12 according to an embodiment controls treatment parameters of focused ultrasound so as to maximally utilize mechanical energy while minimizing thermal increase in the affected area when using an ultrasound treatment method using the mechanical energy.

The treatment parameters may include treatment sequence, intensity, exposure time, duty rate, pulse repetition frequency (PRF) interval, weight (according to a distance, steering, etc.), and the like of focused ultrasound.

When focused ultrasound is intensively focused on a predetermined treatment point, the control unit 12 may adjust the treatment parameters, for example, intensity, exposure time, duty rate, and the like, such that thermal damage to a target region is minimized. In another example, when a treatment point is moved, the control unit 12 sets the treatment parameter, for example, focused ultrasound treatment sequence, such that thermal damage is minimized.

For example, when setting the focused ultrasound treatment sequence, the focused ultrasound device 1 determines diagnostic ultrasound to an object through the transceiver unit 11, receives an ultrasound echo signal reflected from the object, confirms an affected area through an ultrasound image produced based on a reception signal, and then determines a target region to be irradiated with focused ultrasound. The target region corresponds to a site to be treated. Then, a treatment parameter control unit 121 of the control unit 12 sets the focused ultrasound treatment sequence by controlling the treatment parameters, and a focused ultrasound control unit 122 generates a control signal to emit focused ultrasound to a three-dimensional position set through the ultrasound image. Thereafter, the ultrasound generation unit 10 generates focused ultrasound pulses in response to the control signal transmitted from the focused ultrasound control unit 122, and the focused ultrasound converter 111 of the transceiver unit 11 converts the focused ultrasound pulses into an ultrasound signal and emits the ultrasound signal to the site to be treated.

More specifically, the treatment parameter control unit 121 may set the treatment sequence for emitting focused ultrasound such that thermal damage to the target region to be irradiated with focused ultrasound is minimized. In this case, the treatment sequence may include position information of the target region having a next treatment point to be irradiated with focused ultrasound, and a position of the next treatment point may be determined in consideration of at least one previous treatment point position of focused ultrasound. Then, the focused ultrasound control unit 122 generates a control signal to emit focused ultrasound to the position of the next treatment point in the target region according to the set treatment sequence. The focused ultrasound converter 111 of the transceiver unit 11 emits focused ultrasound to the position of the next treatment point in the target region according to the treatment sequence in response to the control signal of the focused ultrasound control unit 122.

The treatment parameter control unit 121 may determine a treatment point candidate with the farthest distance from a previous treatment point as the next treatment point from among a group of a plurality of treatment point candidates. In this case, when there are a plurality of treatment point candidates with the farthest distance from the previous treatment point, the treatment parameter control unit 121 may determine a treatment point candidate at a position with the shortest driving distance of a device (e.g., the focused ultrasound converter) as the next treatment point. Further, the treatment parameter control unit 121 may preset a maximum distance of the next treatment point with respect to a previous treatment point, and then determine the position of the next treatment point within the preset maximum distance.

The treatment parameter control unit 121 may convert distance information between the previous treatment point and the group of next treatment point candidates into temperature information and determine a treatment point candidate at a position having a minimum temperature increase, from among the group of next treatment point candidates, as the next treatment point by using the converted temperature information.

When focused ultrasound is intensively focused on a predetermined treatment point, the treatment parameter control unit 121 may adjust the treatment parameters, for example, intensity, duty rate, exposure time, and the like of the focused ultrasound, such that thermal damage to the target region is minimized.

Figure 2:
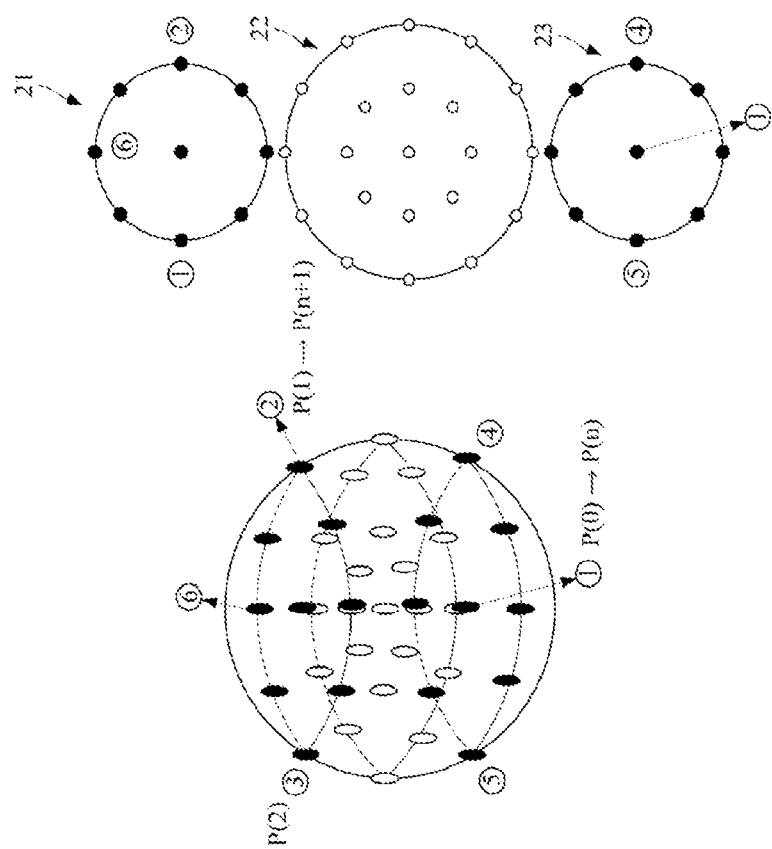
FIG. 2 is a diagram illustrating a three-dimensional structure of a target region for setting a focused ultrasound treatment sequence according to an embodiment of the present invention.

FIG. 2 is a diagram illustrating a three-dimensional structure of a target region for setting a focused ultrasound treatment sequence according to an embodiment of the present invention.

Referring to FIGS. 1 and 2, the focused ultrasound device 1 may convert an ultrasound image of an ultrasound focusing position into three-dimensional structure data, and convert the converted three-dimensional structure into a connection network of points having a predetermined rule on an orthogonal coordinate system. FIG. 2 illustrates three connection networks 21, 22, and 23 as an example. Various points may be created by titling (e.g., 0 degrees, 5 degrees, and 10 degrees) and moving the focused ultrasound converter 111 for each connection network 21, 22, and 23, and various points may be created by rotating and moving the focused ultrasound converter 111. The target region corresponds to a site to be treated which is to be irradiated with focused ultrasound. The orthogonal coordinate system may include a Cartesian coordinate system, a spherical coordinate system, and the like. The predetermined rule may be equidistance, equal angles, or a combination thereof.

The focused ultrasound device 1 according to an embodiment sets a focused ultrasound treatment sequence in consideration of thermal damage by the focused ultrasound in order to minimize thermal damage during ultrasound treatment using mechanical energy.

When the focus needs to be moved to another point in the target region, the focused ultrasound device 1 sets the treatment sequence to emit ultrasound as far as possible from the position to which focused ultrasound is previously emitted such that thermal increase in the previous focused position does not occur. In particular, a position farthest as possible from the latest treatment point may be determined as a next treatment point, which may be called "As Far Away Enough (AFAE) from the latest treatment point method" or "far enough from the latest treatment point (FELT) method." FIG. 2 illustrates an example of emitting focused ultrasound in the treatment sequence of ①→②→③→④→⑤.

Figure 3:
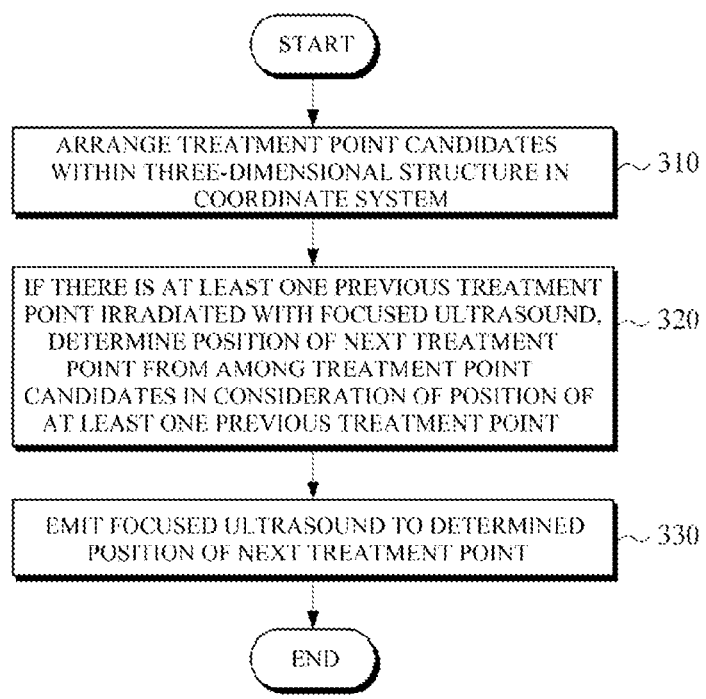
FIG. 3 is a flowchart illustrating a method for setting a focused ultrasound treatment sequence according to an embodiment of the present invention.

FIG. 3 is a flowchart illustrating a method for setting a focused ultrasound treatment sequence according to an embodiment of the present invention.

Referring to FIGS. 1 and 3, as the pre-processing, the focused ultrasound device 1 converts an ultrasound image of a target region into three-dimensional structure data, and converts the converted three-dimensional structure into a connection network of points having a predetermined rule on an orthogonal coordinate system. The target region corresponds to a site to be treated which is to be irradiated with focused ultrasound. The orthogonal coordinate system may include a Cartesian coordinate system, a spherical coordinate system, and the like. The predetermined rule may be equidistance, equal angles, or a combination thereof.

The focused ultrasound device 1 arranges treatment point candidates within the three-dimensional structure in a random order in the coordinate system (310). In this case, the treatment point candidates may be arranged in a random order or according to a preset rule. The predetermined rule may be equidistance, equal angles, or a combination thereof.

Then, the focused ultrasound device 1 determines a position of a treatment point, wherein when there are at least one previous treatment point irradiated with focused ultrasound, the focused ultrasound device 1 determines a position of a next treatment point from among the treatment point candidates in consideration of the position of the at least one treatment point (320). The previous treatment point may be the latest treatment point $PT(0)_n$. In another example, the previous treatment point may include the latest treatment point $PT(0)_n$ and first to Lth treatment points (L=integer) preceding the latest treatment point $PT(0)_n$. L is preset and is changeable by a user. In this case, a different weight may be assigned to each of the previous treatment points. A higher weight may be assigned to a more recent treatment point than to the previous treatment point in temporal order.

In step 320 of determining the position of the next treatment point, when the treatment point is moved, the focused ultrasound device 1 may determine the position of the next treatment point in consideration of a position of at least one previous treatment point of focused ultrasound. For example, the focused ultrasound device 1 may determine a treatment point candidate with the farthest distance from a previous treatment point as the next treatment point from among a plurality of treatment point candidates. In this case, when there are a plurality of treatment point candidates with the farthest distance from the previous treatment point, the focused ultrasound device 1 may determine a treatment point candidate at a position with the shortest driving distance of a device as the next treatment point.

In step 320 of determining the position of the next treatment point, the focused ultrasound device 1 may preset a maximum distance of the next treatment point with respect to the previous treatment point, and then determine the position of the next treatment point within the preset maximum distance.

In step 320 of determining the position of the next treatment point, the focused ultrasound device 1 may convert distance information between the previous treatment point and a group of next treatment point candidates into temperature information and determine a treatment point candidate at a position having a minimum temperature increase, from among the group of next treatment point candidates, as the next treatment point by using the converted temperature information.

In step 320 of setting a treatment sequence, the focused ultrasound device 1 may adjust treatment parameters to minimize thermal damage to a target region when focused ultrasound is intensively focused on a predetermined treatment point. The treatment parameters may include intensity, exposure time, duty rate, pulse repetition frequency (PRF) interval, weight (according to a distance, steering, etc.), and the like of focused ultrasound.

Thereafter, the focused ultrasound device 1 emits focused ultrasound to the determined position of the next treatment point (330).

Figure 4:
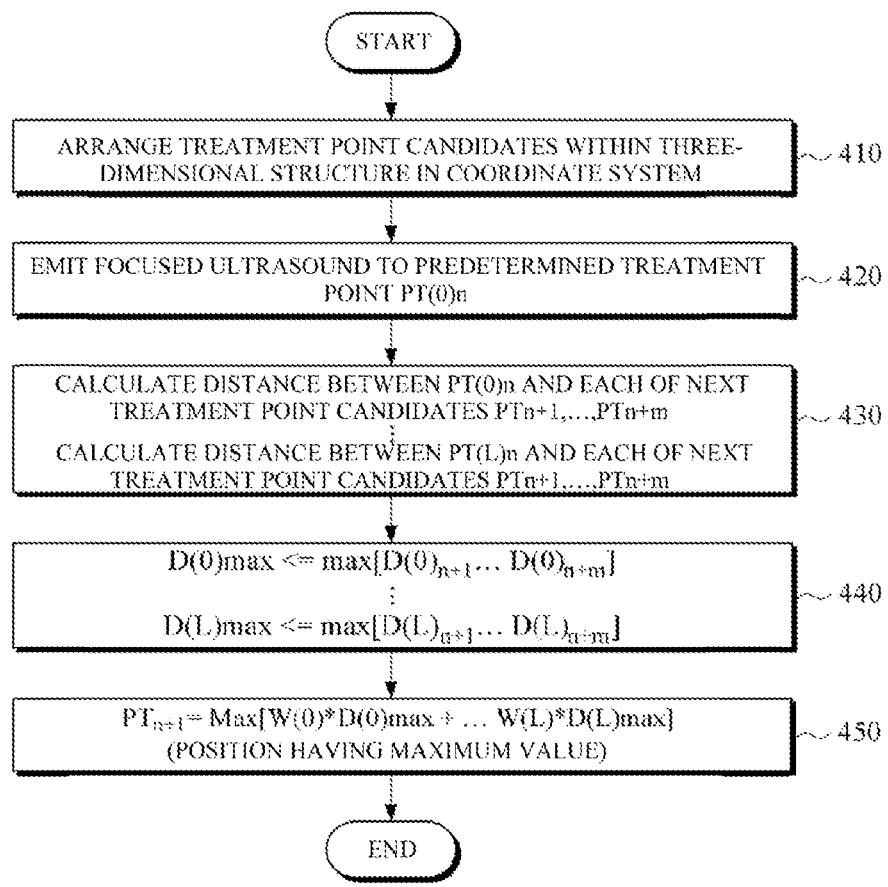
FIG. 4 is a flowchart illustrating a process of positioning a next treatment point in consideration of a distance according to an embodiment of the present invention.

FIG. 4 is a flowchart illustrating a process of determining a position of a next treatment point in consideration of a distance according to an embodiment of the present invention.

To describe a process of positioning a next treatment point after considering a distance, the term "$PT(0)_n$" is defined as the latest treatment point, which is the same point as $PT_n$ ($PT(0)_n=PT_n$). $PT(L)_n$ is an Lth previous treatment point before the latest treatment point $PT(0)_n$. L represents an Lth irradiation before the latest treatment point $PT(0)_n$. For example, treatment point $PT(1)_n$ is the first previous treatment point before the latest treatment point $PT(0)_n$, treatment point $PT(2)_n$ is the second previous treatment point before the latest treatment point $PT(0)_n$, and treatment point $PT(L)_n$ is the Lth previous treatment point before the latest treatment point $PT(0)_n$.

Referring to FIGS. 1 and 4, the focused ultrasound device 1 arranges treatment point candidates within the three-dimensional structure in the coordinate system (410). The structure consists of a connection network in which next treatment point candidates are connected from PTn+1 to PTn+m along a preset trajectory. The trajectory may be arbitrarily set, and may be preset according to an algorithm that determines the treatment sequence.

Subsequently, the focused ultrasound device 1 emits focused ultrasound to a predetermined treatment point $PT(0)_n$ (420).

Then, in order to position a next treatment point, the focused ultrasound device 1 calculates a distance value between each of the next treatment point candidates $PT_{n+1}$ to $PT_{n+m}$ and each previous treatment point along the trajectory (430). For example, the focused ultrasound device 1 calculates a distance value $[D(0)_{n+1}, \ldots, D(0)_{n+m}]$ between the latest treatment point $PT(0)_n$ and each of the next treatment point candidates $[PT_{n+1}, \ldots, PT_{n+m}]$. In addition, the focused ultrasound device 1 calculates a distance value $[D(1)_{n+1}, \ldots, D(1)_{n+m}]$ between the first treatment point $PT(1)_n$, preceding the latest treatment point, and each of the next treatment point candidates $[PT_{n+1}, \ldots, PT_{n+m}]$. In this way, the focused ultrasound device 1 calculates up to a distance value $[D(L)_{n+1}, \ldots, D(L)_{n+m}]$ between the Lth treatment point $PT(L)_n$, preceding the latest treatment point $PT(0)_n$, and each of the next treatment point candidates $[D(L)_{n+1}, \ldots, D(L)_{n+m}]$. To sum up, the focused ultrasound device 1 calculates $$\begin{bmatrix} D(0)_{n+1} & \cdots & D(0)_{n+m} \\ \vdots & \ddots & \vdots \\ D(L)_{n+1} & \cdots & D(L)_{n+m} \end{bmatrix}.$$

Then, the focused ultrasound device 1 calculates a maximum distance $[D(0)_{max}, \ldots, D(L)_{max}]$ (440). $D(0)_{max}$ is the maximum value among $[D(0)_{n+1}, \ldots, D(0)_{n+m}]$, i.e., $\max[D(0)_{n+1}, \ldots, D(0)_{n+m}]$, and is the farthest distance value from the latest treatment point $PT(0)_n$. $D(L)_{max}$ is the maximum value among $[D(L)_{n+1}, \ldots, D(L)_{n+m}]$, i.e., $\max[D(L)_{n+1}, \ldots, D(L)_{n+m}]$, and is the farthest distance value from the Lth previous treatment point $PT(L)_n$.

Then, the focused ultrasound device 1 assigns a weight to each maximum value $[D(0)_{max}, \ldots, D(L)_{max}]$, then calculates the summation distance $[W(0)*D(0)_{max}+\ldots+, W(L)*D(L)_{max}]$ by summing up the weighted maximum values, and determines a position having the maximum summation distance $\max[W(0)*D(0)_{max}+\ldots+, W(L)*D(L)_{max}]$ (coordinate value of the farthest point) as the position of the next treatment point (450). Here, $W(0), \ldots$ and, $W(L)$ each represents a weight and is a real number smaller than 1 and greater or smaller than 0. A higher weight may be assigned to a more recent treatment point than to an older treatment point among the previous treatment points, and the weight may be changed by a user.

Figure 5:
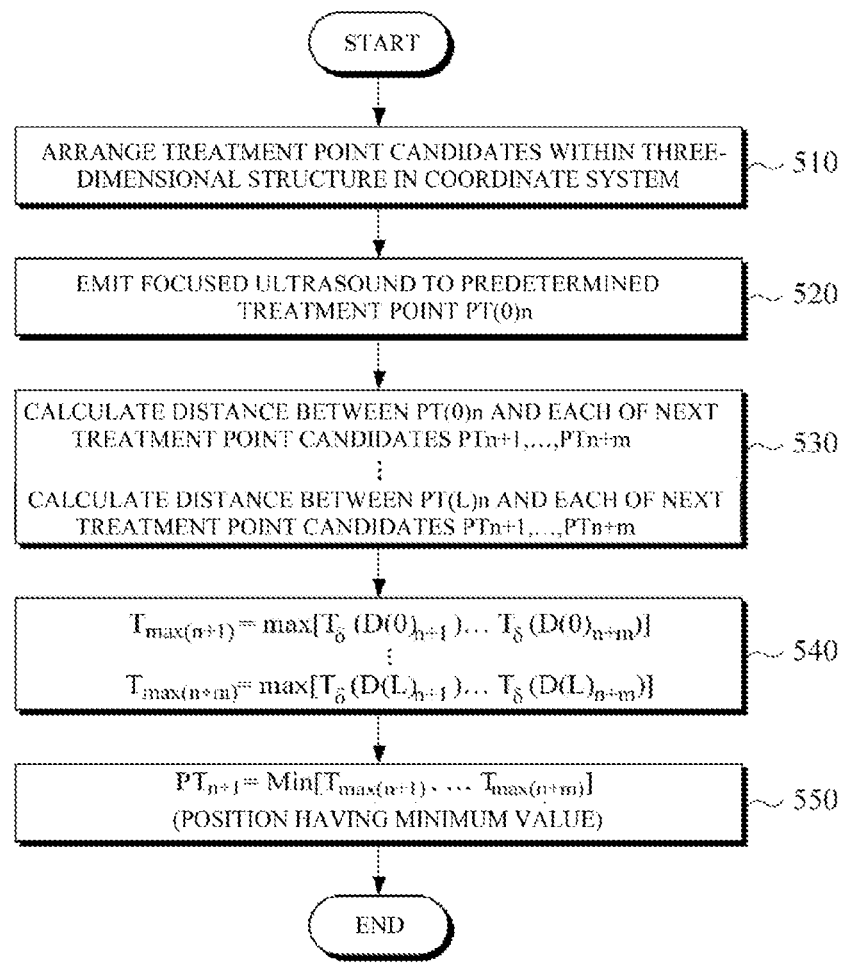
FIG. 5 is a flowchart illustrating a process of positioning a next treatment point in consideration of temperature according to an embodiment of the present invention.

FIG. 5 is a flowchart illustrating a process of positioning a next treatment point in consideration of temperature according to an embodiment of the present invention.

To describe a process of positioning a next treatment point after considering temperature, the term "$PT(0)_n$" is defined as the latest treatment point, which is the same point as $PT_n$($PT(0)_n=PT_n$). $PT(L)_n$ is an Lth previous treatment point before the latest treatment point $PT(0)_n$. L represents an Lth irradiation before the latest treatment point $PT(0)_n$. For example, treatment point $PT(1)_n$ is a first previous treatment point that is the first preceding treatment point before the latest treatment point $PT(0)_n$, treatment point $PT(2)_n$ is a second previous treatment point that is the second preceding treatment point before the latest treatment point $PT(0)_n$, and treatment point $PT(L)_n$ is an Lth previous treatment point that is the Lth preceding treatment point before the latest treatment point $PT(0)_n$.

Subsequently, the focused ultrasound device 1 emits focused ultrasound to a predetermined treatment point $PT(0)_n$ (420).

Then, in order to position a next treatment point, the focused ultrasound device 1 calculates a distance value between each of the next treatment point candidates $PT_{n+1}$ to $PT_{n+m}$ and each previous treatment point along the trajectory (430). For example, the focused ultrasound device 1 calculates a distance value $[D(0)_{n+1}, \ldots, D(0)_{n+m}]$ between the latest treatment point $PT(0)_n$ and each of the next treatment point candidates $[PT_{n+1}, \ldots, PT_{n+m}]$. In addition, the focused ultrasound device 1 calculates a distance value $[D(1)_{n+1}, \ldots, D(1)_{n+m}]$ between the first treatment point $PT(1)_n$, preceding the latest treatment point, and each of the next treatment point candidates $[PT_{n+1}, \ldots, PT_{n+m}]$. In this way, the focused ultrasound device 1 calculates up to a distance value $[D(L)_{n+1}, \ldots, D(L)_{n+m}]$ between the Lth treatment point $PT(L)_n$, preceding the latest treatment point $PT(0)_n$, and each of the next treatment point candidates $[D(L)_{n+1}, \ldots, D(L)_{n+m}]$. To sum up, the focused ultrasound device 1 calculates $$\begin{bmatrix} D(0)_{n+1} & \cdots & D(0)_{n+m} \\ \vdots & \ddots & \vdots \\ D(L)_{n+1} & \cdots & D(L)_{n+m} \end{bmatrix}.$$

Then, the focused ultrasound device 1 calculates a maximum distance $[D(0)_{max}, \ldots, D(L)_{max}]$ (440). $D(0)_{max}$ is the maximum value among $[D(0)_{n+1}, \ldots, D(0)_{n+m}]$, i.e., $\max[D(0)_{n+1}, \ldots, D(0)_{n+m}]$, and is the farthest distance value from the latest treatment point $PT(0)_n$. $D(L)_{max}$ is the maximum value among $[D(L)_{n+1}, \ldots, D(L)_{n+m}]$, i.e., $\max[D(L)_{n+1}, \ldots, D(L)_{n+m}]$, and is the farthest distance value from the Lth previous treatment point $PT(L)_n$.

Then, the focused ultrasound device 1 assigns a weight to each maximum value $[D(0)_{max}, \ldots, D(L)_{max}]$, then calculates the summation distance $[W(0)*D(0)_{max} + \ldots + W(L)*D(L)_{max}]$ by summing up the weighted maximum values, and determines a position having the maximum summation distance $\max[W(0)*D(0)_{max} + \ldots + W(L)*D(L)_{max}]$ (coordinate value of the farthest point) as the position of the next treatment point (450). Here, $W(0), \ldots$ and, $W(L)$ each represents a weight and is a real number smaller than 1 and greater or smaller than 0. A higher weight may be assigned to a more recent treatment point than to an older treatment point among the previous treatment points, and the weight may be changed by a user.

FIG. 5 is a flowchart illustrating a process of positioning a next treatment point in consideration of temperature according to an embodiment of the present invention.

To describe a process of positioning a next treatment point after considering temperature, the term "$PT(0)_n$" is defined as the latest treatment point, which is the same point as $PT_n(PT(0)_n = PT_n)$. $PT(L)_n$ is an Lth previous treatment point before the latest treatment point $PT(0)_n$. L represents an Lth irradiation before the latest treatment point $PT(0)_n$. For example, treatment point $PT(1)_n$ is a first previous treatment point that is the first preceding treatment point before the latest treatment point $PT(0)_n$, treatment point $PT(2)_n$ is a second previous treatment point that is the second preceding treatment point before the latest treatment point $PT(0)_n$, and treatment point $PT(L)_n$ is an Lth previous treatment point that is the Lth preceding treatment point before the latest treatment point $PT(0)_n$.

Referring to FIGS. 1 and 4, the focused ultrasound device 1 arranges treatment point candidates within the three-dimensional structure in the coordinate system (510). The structure consists of a connection network in which next treatment point candidates are connected from $PT_{n+1}$ to $PT_{n+m}$ along a preset trajectory. The trajectory may be arbitrarily set, and may be preset according to an algorithm that determines the treatment sequence.

Subsequently, the focused ultrasound device 1 emits focused ultrasound to a predetermined treatment point $PT(0)_n$ (520).

Then, in order to position a next treatment point, the focused ultrasound device 1 calculates a distance value between each of the next treatment point candidates $PT_{n+1}$ to $PT_{n+m}$ and each previous treatment point along the trajectory (530). For example, the focused ultrasound device 1 calculates a distance value $[D(0)_{n+1}, \ldots, D(0)_{n+m}]$ between the latest treatment point $PT(0)_n$ and each of the next treatment point candidates $[PT_{n+1}, \ldots, PT_{n+m}]$. In addition, the focused ultrasound device 1 calculates a distance value $[D(1)_{n+1}, \ldots, D(1)_{n+m}]$ between the first treatment point $PT(1)_n$, preceding the latest treatment point, and each of the next treatment point candidates $[PT_{n+1}, \ldots, PT_{n+m}]$. In this way, the focused ultrasound device 1 calculates up to a distance value $[D(L)_{n+1}, \ldots, D(L)_{n+m}]$ between the Lth treatment point $PT(L)_n$, preceding the latest treatment point $PT(0)_n$, and each of the next treatment point candidates $[PT_{n+1}, \ldots, PT_{n+m}]$. To sum up, the focused ultrasound device 1 calculates $$\begin{bmatrix} D(0)_{n+1} & \cdots & D(0)_{n+m} \\ \vdots & \ddots & \vdots \\ D(L)_{n+1} & \cdots & D(L)_{n+m} \end{bmatrix}.$$

Thereafter, the focused ultrasound device 1 calculates a temperature value $$\begin{bmatrix} T_\delta D(0)_{n+1} & \cdots & T_\delta D(0)_{n+m} \\ \vdots & \ddots & \vdots \\ T_\delta D(L)_{n+1} & \cdots & T_\delta D(L)_{n+m} \end{bmatrix}$$

by converting the distance value into a temperature value. $T_\delta$ is a temperature change value during an irradiation time $\delta t$ under preset irradiation conditions. In this case, the temperature change value may be obtained through focused ultrasound irradiation, and the temperature change value may be obtained through a simulation based on the fact that the temperature is inversely proportional to the distance.

Then, the focused ultrasound device 1 calculates a maximum temperature $[T_{max(n+1)}, \ldots, T_{max(n+m)}]$ (540). Here, $T\max(n+1)$ is the maximum value $\max[T_\delta D(0)_{n+1}, T_\delta D(0)_{n+m}]$, $T\max_{(n+m)}$ is the maximum value $\max[T_\delta D(L)_{n+1}, T_\delta D(L)_{n+m}]$, and $T_\delta$ is the temperature change value during the irradiation time $\delta t$.

Thereafter, the focused ultrasound device 1 determines a position having the minimum value Min[$T_{max(n+1)}$, $T_{max(n+2)}$, $T_{max(n+3)}$, ..., $T_{max(n+m)}$] (coordinate value of a point with the smallest temperature change) as the position of the next treatment point (550). Step 550 may be repeated m times, and, if the temperature change value is less than a preset temperature value, the corresponding treatment point may be ultimately determined as the next treatment point.

Figure 6:
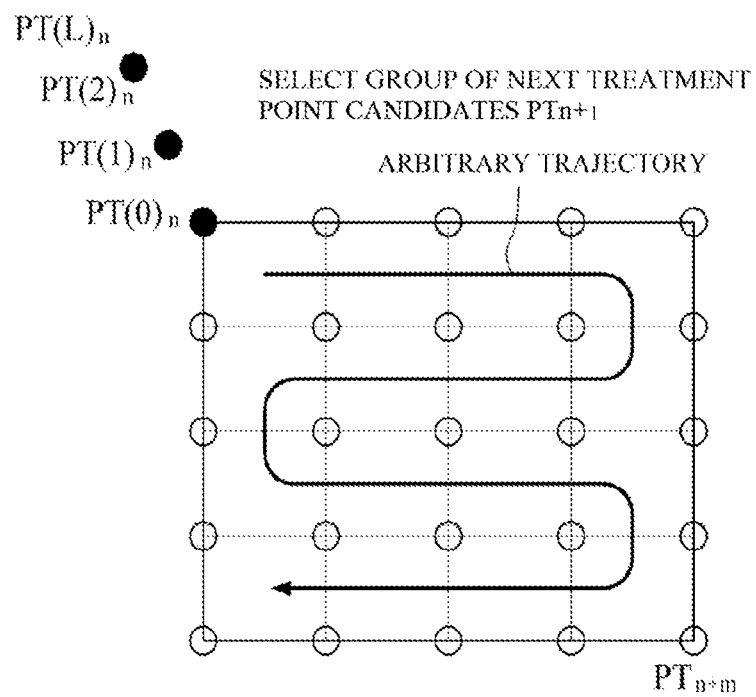
FIG. 6 is a diagram of a structure obtained by two-dimensionally analyzing a three-dimensional structure of a target region to describe a method of positioning a next treatment point in consideration of a distance and a method of positioning a next treatment point in consideration of a distance and temperature, in accordance with an embodiment of the present invention.

FIG. 6 is a diagram of a structure obtained by two-dimensionally analyzing a three-dimensional structure of a target region to describe a method of positioning a next treatment point in consideration of a distance and a method of positioning a next treatment point in consideration of a distance and temperature, in accordance with an embodiment of the present invention.

A structure consists of a connection network in which next treatment point candidates are connected from $PT_{n+1}$ to $PT_{n+m}$ along a preset trajectory. The trajectory may be arbitrarily set, and may be preset according to an algorithm that determines the treatment sequence. The term "$PT(0)_n$" is defined as the latest treatment point, which is the same point as $PT_n$ ($PT(0)_n = PT_n$). $PT(L)_n$ is an Lth previous treatment point before the latest treatment point $PT(0)_n$. L represents an Lth irradiation before the latest treatment point $PT(0)_n$. For example, treatment point $PT(1)_n$ is a first previous treatment point that is the first preceding treatment point before the latest treatment point $PT(0)_n$, treatment point $PT(2)_n$ is a second previous treatment point that is the second preceding treatment point before the latest treatment point $PT(0)_n$, and treatment point $PT(L)_n$ is an Lth previous treatment point that is the Lth preceding treatment point before the latest treatment point $PT(0)_n$.

A process of positioning a next treatment point using a distance will be described with reference to the structure shown in FIG. 6.

Referring to FIGS. 1 and 6, in order to position a next treatment point, the focused ultrasound device 1 calculates a distance value between each of the next treatment point candidates $PT_{n+1}$ to $PT_{n+m}$ and each previous treatment point along the trajectory. For example, the focused ultrasound device 1 calculates a distance value [$D(0)_{n+1}$, ..., $D(0)_{n+m}$] between the latest treatment point $PT(0)_n$ and each of the next treatment point candidates [$PT_{n+1}$, ..., $PT_{n+m}$]. In addition, the focused ultrasound device 1 calculates a distance value [$D(L)_{n+1}$, ..., $D(L)_{n+m}$] between the Lth treatment point $PT(L)_n$, preceding the latest treatment point $PT(0)_n$, and each of the next treatment point candidates [$PT_{n+1}$, ..., $PT_{n+m}$].

$$D(0)_{n+1} = |PT_{n+1} - PT(0)_n|, D(1)_{n+1} = |PT_{n+1} - PT(1)_n|, \ldots, D(L)_{n+1} = |PT_{n+1} - PT(L)_n|,$$

$$D(0)_{n+2} = |PT_{n+2} - PT(0)_n|, D(1)_{n+2} = |PT_{n+2} - PT(1)_n|, \ldots, D(L)_{n+2} = |PT_{n+2} - PT(L)_n|,$$

$$D(0)_{n+m} = |PT_{n+m} - PT(0)_n|, D(1)_{n+m} = |PT_{n+m} - PT(1)_n|, \ldots, D(L)_{n+m} = |PT_{n+m} - PT(L)_n|$$

Then, the focused ultrasound device 1 calculates a maximum distance [$D(0)_{max}$, ..., $D(L)_{max}$]. $D(0)_{max}$ is the maximum value among [$D(0)_{n+1}$, ..., $D(0)_{n+m}$], i.e., max[$D(0)_{n+1}$, ..., $D(0)_{n+m}$], and is the farthest distance value from the latest treatment point $PT(0)_n$. $D(L)_{max}$ is the maximum value among [$D(L)_{n+1}$, ..., $D(L)_{n+m}$], i.e., max[$D(L)_{n+1}$, ..., $D(L)_{n+m}$], and is the farthest distance value from the Lth previous treatment point $PT(L)_n$.

Then, the focused ultrasound device 1 assigns a weight to each maximum value [$D(0)_{max}$, ..., $D(L)_{max}$], then calculates the summation distance [$W(0)*D(0)_{max} + \ldots +$, $W(L)*D(L)_{max}$] by summing up the weighted maximum values, and determines a position having the maximum summation distance max[$W(0)*D(0)_{max} + \ldots +$, $W(L)*D(L)_{max}$] (coordinate value of the farthest point) as the position of the next treatment point (450). Here, W(0), ... and, W(L) each represents a weight and is a real number smaller than 1 and greater or smaller than 0. A higher weight may be assigned to a more recent treatment point than to an older treatment point among the previous treatment points, and the weight may be changed by a user.

As another example, a process of positioning a next treatment point using temperature will be described with reference to the structure shown in FIG. 6.

Referring to FIGS. 1 and 6, in order to position a next treatment point, the focused ultrasound device 1 calculates a distance value between each of the next treatment point candidates $PT_{n+1}$ to $PT_{n+m}$ and each previous treatment point along the trajectory. For example, the focused ultrasound device 1 calculates a distance value [$D(0)_{n+1}$, ..., $D(0)_{n+m}$] between the latest treatment point $PT(0)_n$ and each of the next treatment point candidates [$PT_{n+1}$, ..., $PT_{n+m}$]. In addition, the focused ultrasound device 1 calculates a distance value [$D(L)_{n+1}$, ..., $D(L)_{n+m}$] between the Lth treatment point $PT(L)_n$, preceding the latest treatment point $PT(0)_n$, and each of the next treatment point candidates [$PT_{n+1}$, ..., $PT_{n+m}$].

$$D(0)_{n+1} = |PT_{n+1} - PT(0)_n|, D(1)_{n+1} = |PT_{n+1} - PT(1)_n|, \ldots, D(L)_{n+1} = |PT_{n+1} - PT(L)_n|,$$

$$D(0)_{n+2} = |PT_{n+2} - PT(0)_n|, D(1)_{n+2} = |PT_{n+2} - PT(1)_n|, \ldots, D(L)_{n+2} = |PT_{n+2} - PT(L)_n|,$$

$$D(0)_{n+m} = |PT_{n+m} - PT(0)_n|, D(1)_{n+m} = |PT_{n+m} - PT(1)_n|, \ldots, D(L)_{n+m} = |PT_{n+m} - PT(L)_n|$$

Thereafter, the focused ultrasound device 1 calculates a temperature value $$\begin{bmatrix} T_\delta D(0)_{n+1} & \cdots & T_\delta D(0)_{n+m} \\ \vdots & \ddots & \vdots \\ T_\delta D(L)_{n+1} & \cdots & T_\delta D(L)_{n+m} \end{bmatrix}$$

by converting the distance value into a temperature value. $T\delta$ is a temperature change value during an irradiation time $\delta t$ under preset irradiation conditions. In this case, the temperature change value may be obtained through focused ultrasound irradiation, and the temperature change value may be obtained through a simulation based on the fact that the temperature is inversely proportional to the distance.

Then, the focused ultrasound device 1 calculates a maximum temperature [$T_{max(n+1)}$, ..., $T_{max(n+m)}$]. Here, $T_{max(n+1)}$ is the maximum value max[$T_\delta D(0)_{n+1}$, ..., $T_\delta D(0)_{n+m}$], $T_{max(n+m)}$ is the maximum value max[$T_\delta D(L)_{n+1}$, ..., $T_\delta D(L)_{n+m}$], and $T_\delta$ is the temperature change value during the irradiation time $\delta t$.

Thereafter, the focused ultrasound device 1 determines a position having the minimum value Min[$T_{max(n+1)}$, $T_{max(n+2)}$, $T_{max(n+3)}$, ..., $T_{max(n+m)}$] (coordinate value of a point with the smallest temperature change) as the position of the next treatment point. The above operation may be repeated m times, and, if the temperature change value is less than a preset temperature value, the corresponding treatment point may be ultimately determined as the next treatment point.

Figure 7:
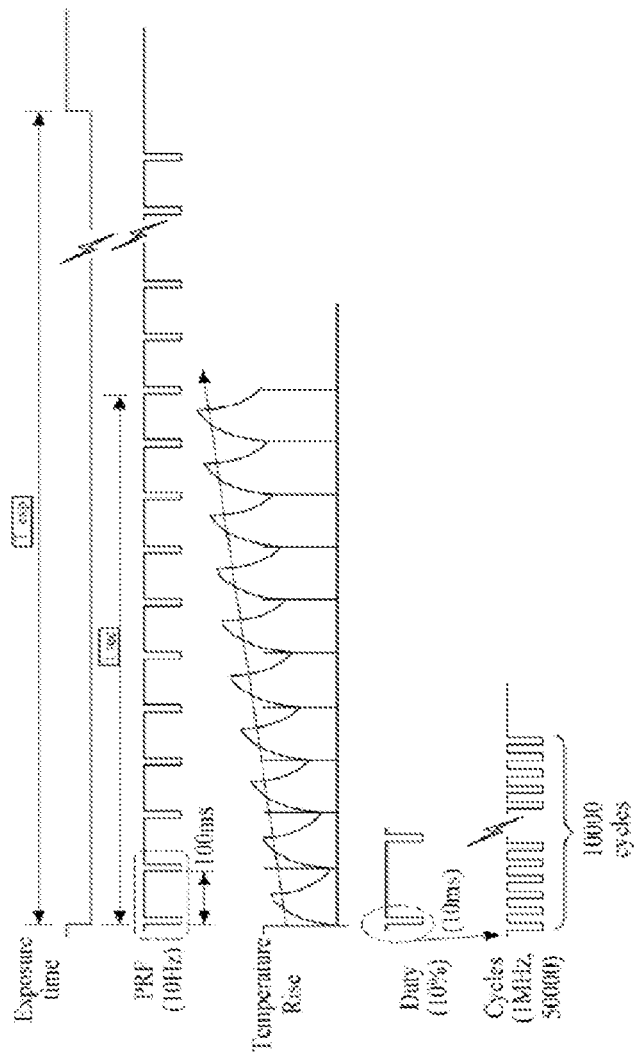
FIGS. 7 and 8 are diagrams illustrating an effect of emitting focused ultrasound in consideration of a position of a previous treatment point according to an embodiment of the present invention.
Figure 8:
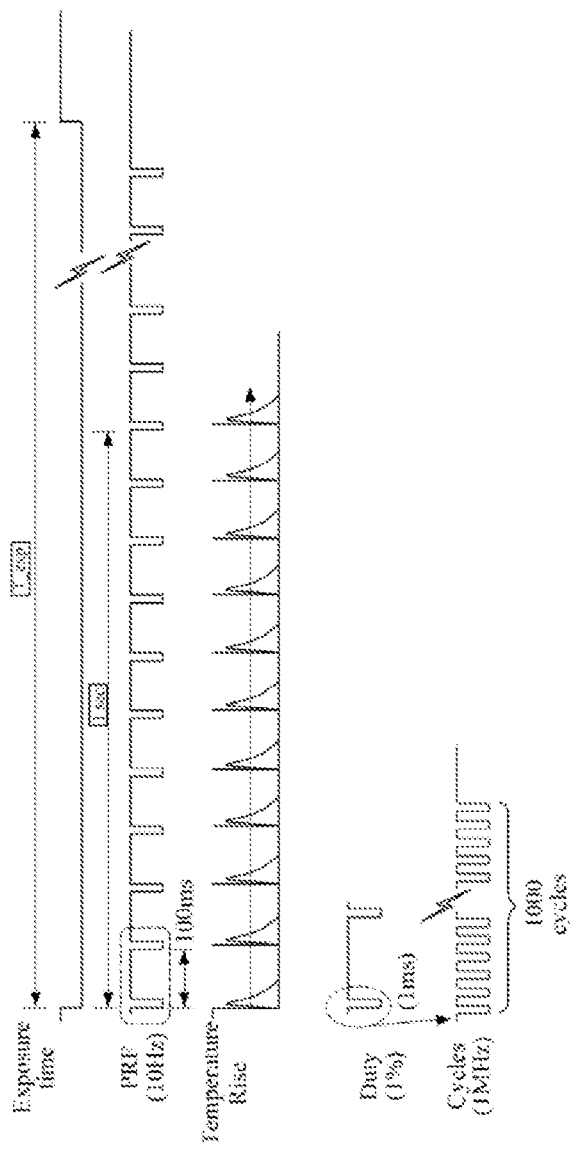

FIGS. 7 and 8 are diagrams illustrating an effect of emitting focused ultrasound in consideration of a position of a previous treatment point according to an embodiment of the present invention.

More specifically, FIG. 7 is a diagram illustrating a case where thermal increase occurs in an affected area when irradiated with focused ultrasound without considering a position of a previous treatment point, and FIG. 8 is a diagram illustrating a case where thermal increase in an affected area is prevented when irradiated with focused ultrasound in consideration of a position of a previous treatment point according to an embodiment of the present invention.

According to an embodiment, when using an ultrasound treatment method for the purpose of simulating the affected area or improving the delivery effect of a therapeutic drug by using mechanical energy, rather than thermal therapy, it is possible to minimize thermal increase of an affected area and maximally utilize the mechanical energy. For example, a next treatment point position is determined in consideration of at least one previous treatment point position of focused ultrasound and thus thermal increase in an affected area can be minimized.

Heretofore, the present invention has been described by focusing on the exemplary embodiments. It can be understood by those skilled in the art to which the present invention pertains that the present invention can be implemented in modified forms without departing from the essential feature of the present invention. Therefore, the disclosed embodiments should be considered as illustrative rather than determinative. The scope of the present invention is defined by the appended claims rather than by the foregoing description, and all differences within the scope of equivalents thereof should be construed as being included in the present invention.

INDUSTRIAL AVAILABILITY

The present invention can be efficiently applied to a technique for determining the safest position in consideration of previous treatment position information when selecting a position according to a treatment sequence, in order to select a treatment location to minimize damage such as thermal damage or radiation exposure of energy or material (e.g., focused ultrasound) for the purpose of treatment.

The invention claimed is:

1. A method for setting a focused ultrasound treatment sequence using a focused ultrasound device for image guided therapy, the method comprising:
by the focused ultrasound device, arranging treatment point candidates within a three-dimensional structure in a coordinate system;
determining a position of a next treatment point by a controller configured to arrange treatment point candidates within a three-dimensional structure in a coordinate system and, if there is at least one previous treatment point irradiated with focused ultrasound, determine the position of the next treatment point among the treatment point candidates in consideration of a position of the at least one previous treatment point; and
emitting focused ultrasound to the determined position of the next treatment point,
wherein the determining of the position of the next treatment point comprises:
calculating a distance value $$\begin{bmatrix} D(0)_{n+1} & \cdots & D(0)_{n+m} \\ \vdots & \ddots & \vdots \\ D(L)_{n+1} & \cdots & D(L)_{n+m} \end{bmatrix};$$

calculating a maximum distance $[D(0)_{max}, \ldots, D(L)_{max}]$; and
determining a position having a maximum value $\max[W(0)*D(0)_{max} + \ldots + W(L)*D(L)_{max}]$ as the position of the next treatment point,
wherein $[D(0)_{n+1}, \ldots, D(0)_{n+m}]$ is a distance between a latest treatment point $PT(0)_n$ and each of the next treatment point candidates $[PT_{n+1}, \ldots, PT_{n+m}]$,
$[D(L)_{n+1}, \ldots, D(L)_{n+m}]$ is a distance between an Lth treatment point $PT(L)_n$, preceding the latest treatment point $PT(0)_n$, and each of the next treatment point candidates $[PT_{n+1}, \ldots, PT_{n+m}]$, $D(0)_{max}$ is $\max[D(0)_{n+1}, \ldots, D(0)_{n+m}]$,
$D(L)_{max}$ is $\max[D(L)_{n+1}, \ldots, D(L)_{n+m}]$,
$W(0), \ldots,$ and $W(L)$ each is a weight,
L represents an Lth irradiation before the latest treatment point $PT(0)_n$,
n represents nth point, and
m represents mth point.

2. The method of claim 1, wherein in the determining of the position of the next treatment point, when there are treatment point candidates with a farthest distance from the previous treatment point, a treatment point candidate at a position with a shortest driving distance of the focused ultrasound device is determined as the next treatment point.

3. The method of claim 1, wherein in the determining of the position of the next treatment point, after presetting a maximum distance of the next treatment point with respect to the previous treatment point, the position of the next treatment point is determined within the preset maximum distance.

4. The method of claim 1, wherein the determining of the position of the next treatment point comprises:
converting distance information between the previous treatment point and next treatment points into temperature information; and
determining a treatment point candidate at a position having a minimum temperature increase as the next treatment point from among next treatment point candidates.

5. A method for setting a focused ultrasound treatment sequence using a focused ultrasound device for image guided therapy, the method comprising:
by the focused ultrasound device, arranging treatment point candidates within a three-dimensional structure in a coordinate system;
determining a position of a next treatment point by a controller configured to arrange treatment point candidates within a three-dimensional structure in a coordinate system and, if there is at least one previous treatment point irradiated with focused ultrasound, determine the position of the next treatment point among the treatment point candidates in consideration of a position of the at least one previous treatment point; and
emitting focused ultrasound to the determined position of the next treatment point,
wherein the determining of the position of the next treatment point comprises:
calculating a distance value $$\begin{bmatrix} D(0)_{n+1} & \cdots & D(0)_{n+m} \\ \vdots & \ddots & \vdots \\ D(L)_{n+1} & \cdots & D(L)_{n+m} \end{bmatrix};$$

calculating a temperature value $$\begin{bmatrix} T_\delta D(0)_{n+1} & \cdots & T_\delta D(0)_{n+m} \\ \vdots & \ddots & \vdots \\ T_\delta D(L)_{n+1} & \cdots & T_\delta D(L)_{n+m} \end{bmatrix}$$

converted from the distance value;
calculating a maximum temperature $[T_{max(n+1)}, \ldots, T_{max(n+m)}]$; and
determining a position having a minimum value Min $[T_{max(n+1)}, T_{max(n+2)}, T_{max(n+3)}, \ldots, T_{max(n+m)}]$ as the position of the next treatment point,
wherein $[D(0)_{n+1}, \ldots, D(0)_{n+m}]$ is a distance between a latest treatment point $PT(0)_n$ and each of the next treatment point candidates $[PT_{n+1}, \ldots, PT_{n+m}]$,
$[D(L)_{n+1}, \ldots, D(L)_{n+m}]$ is a distance between an Lth treatment point $PT(L)_n$, preceding the latest treatment point $PT(0)_n$, and each of the next treatment point candidates $[PT_{n+1}, \ldots, PT_{n+m}]$,
$T_{max(n+1)}$ is a maximum value $\max[T_\delta D(0)_{n+1}, \ldots, T_\delta D(0)_{n+m}]$,
$T_{max(n+m)}$ is a maximum value $\max[T_\delta D(L)_{n+1}, \ldots, T_\delta D(L)_{n+m}]$,
$T_\delta$ is a temperature change value during an irradiation time $\delta t$,
L represents an Lth irradiation before the latest treatment point $PT(0)_n$,
n represents nth point, and
m represents mth point.

6. The method of claim 5, wherein the determining of the position of the next treatment point further comprises, if the temperature change value is less than a preset temperature value when the determined next treatment point is irradiated with focused ultrasound, ultimately determining the irradiated treatment point as the next treatment point.

7. The method of claim 1, further comprising:
adjusting treatment parameters to minimize thermal damage to a target region when focused ultrasound is intensively focused on a same treatment point.

8. A focused ultrasound device for image guided therapy comprising:
a control unit configured to arrange treatment point candidates within a three-dimensional structure in a coordinate system and, if there is at least one previous treatment point irradiated with focused ultrasound, determine a position of a next treatment point among the treatment point candidates in consideration of a position of the at least one previous treatment point; and
a transceiver configured to emit focused ultrasound to the determined position of the treatment point,
wherein the control unit comprises:
to calculate distance value $$\begin{bmatrix} D(0)_{n+1} & \cdots & D(0)_{n+m} \\ \vdots & \ddots & \vdots \\ D(L)_{n+1} & \cdots & D(L)_{n+m} \end{bmatrix};$$

to calculate a maximum distance $[D(0)_{max}, \ldots, D(L)_{max}]$; and
to determine a position having a maximum value $\max[W(0)*D(0)_{max} + \ldots + W(L)*D(L)_{max}]$ as the position of the next treatment point,
wherein $[D(0)_{n+1}, \ldots, D(0)_{n+m}]$ is a distance between a latest treatment point $PT(0)_n$ and each of the next treatment point candidates $[PT_{n+1}, \ldots, PT_{n+m}]$,
$D(L)_{n+1}, \ldots, D(L)_{n+m}$ is a distance between an Lth treatment point $PT(L)_n$, preceding the latest treatment point $PT(0)_n$, and each of the next treatment point candidates $[PT_{n+1}, \ldots, PT_{n+m}]$,
$D(0)_{max}$ is $\max[D(0)_{n+1}, \ldots, D(0)_{n+m}]$,
$D(L)_{max}$ is $\max D(L)_{n+1}, \ldots, D(L)_{n+m}]$,
$W(0), \ldots,$ and $W(L)$ each is a weight,
L represents an Lth irradiation before the latest treatment point $PT(0)_n$,
n represents nth point, and
m represents mth point.

9. The focused ultrasound device of claim 8, wherein when there are treatment point candidates with a farthest distance from the previous treatment point, the control unit is configured to determine a treatment point candidate at a position with a shortest driving distance of the focused ultrasound device as the next treatment point.

10. The focused ultrasound device of claim 8, wherein the control unit is configured to preset a maximum distance of the next treatment point with respect to a previous treatment point and then determine the position of the next treatment point within the preset maximum distance.

11. The focused ultrasound device of claim 8, wherein the control unit is configured to convert distance information between the previous treatment point and a group of next treatment point candidates into temperature information and determine a treatment point candidate at a position having a minimum temperature increase, from among the next treatment point candidates, as the next treatment point by using the converted temperature information.

12. The focused ultrasound device of claim 8, wherein the control unit is configured to adjust treatment parameters to minimize thermal damage to a target region when focused ultrasound is intensively focused on a predetermined treatment point.

\* \* \* \* \*